US008197850B2

(12) United States Patent
Castan et al.

(10) Patent No.: US 8,197,850 B2
(45) Date of Patent: Jun. 12, 2012

(54) MEDICINE BASED ON ANTI-HYPERGLYCAEMIC MICROCAPSULES WITH PROLONGED RELEASE AND METHOD FOR PREPARING SAME

(75) Inventors: Catherine Castan, Orlienas (FR); Remi Meyrueix, Lyons (FR); Gerard Soula, Meyzieu (FR)

(73) Assignee: Flamel Technologies (FR)

( * ) Notice: Subject to any disclaimer, the term of this patent is extended or adjusted under 35 U.S.C. 154(b) by 990 days.

(21) Appl. No.: 10/415,850

(22) PCT Filed: Nov. 19, 2001

(86) PCT No.: PCT/FR01/03625
§ 371 (c)(1),
(2), (4) Date: Jun. 6, 2003

(87) PCT Pub. No.: WO02/39984
PCT Pub. Date: May 23, 2002

(65) Prior Publication Data
US 2004/0175424 A1    Sep. 9, 2004

(30) Foreign Application Priority Data

Nov. 17, 2000  (FR) ...................................... 00 14876

(51) Int. Cl.
*A61K 9/14* (2006.01)
(52) U.S. Cl. ........ 424/489; 424/490; 424/493; 424/494; 424/464; 424/470; 424/451; 424/458; 424/459; 424/460; 424/461; 424/457; 564/233
(58) Field of Classification Search .................. None
See application file for complete search history.

(56) References Cited

U.S. PATENT DOCUMENTS

| 4,572,912 | A |   | 2/1986  | Yoshioka et al. |
| 4,639,436 | A |   | 1/1987  | Junge et al. |
| 4,904,769 | A |   | 2/1990  | Rauenbusch |
| 5,594,016 | A |   | 1/1997  | Ueno et al. |
| 5,651,990 | A | * | 7/1997  | Takada et al. ................. 424/497 |
| 5,922,769 | A |   | 7/1999  | Barelli et al. |
| 6,022,562 | A |   | 2/2000  | Autant et al. ................. 424/489 |
| 6,099,862 | A |   | 8/2000  | Chen et al. |
| 6,303,146 | B1|   | 10/2001 | Bonhomme et al. |
| 6,428,809 | B1|   | 8/2002  | Abrams et al. |
| 6,475,521 | B1|   | 11/2002 | Timmins et al. |
| 2003/0064108 | A1 | | 4/2003 | Lukas et al. |
| 2003/0220399 | A1 | | 11/2003 | Luskey et al. |
| 2004/0219212 | A1 | | 11/2004 | Castan et al. |

FOREIGN PATENT DOCUMENTS

| EP | 0 502 642   | 9/1992  | ........................ 9/50 |
| EP | 0 974 356   | 1/2000  |   |
| JP | 2000085159  | 3/2000  |   |
| WO | WO 96/11675 | 4/1996  |   |
| WO | 98/55107    | 12/1998 | ........................ 9/20 |
| WO | 99/47125    | 9/1999  | ........................ 9/20 |
| WO | 99/47128    | 9/1999  | ........................ 9/24 |
| WO | 00/28989    | 5/2000  | ........................ 31/353 |
| WO | WO 00/40233 | 7/2000  |   |
| WO | WO 01/21159 | 3/2001  |   |
| WO | WO 01/32157 | 5/2001  |   |
| WO | WO 01/32158 | 5/2001  |   |
| WO | WO 02/094285| 11/2002 |   |

OTHER PUBLICATIONS

Int'l Search Report dated May 8, 2002; Appl. PCT/FR01/03625.
In the U.S. Patent and Trademark Office, Non-Final Office Action in re: U.S. Appl. No. 10/478,420, dated Jan. 11, 2010, 29 pages.
In the U.S. Patent and Trademark Office, Final Office Action in re: U.S. Appl. No. 10/478,420, dated Jul. 1, 2009, 27 pages.
In the U.S. Patent and Trademark Office, Non-Final Office Action in re: U.S. Appl. No. 10/478,420, dated Sep. 30, 2008, 17 pages.
In the U.S. Patent and Trademark Office, Restriction Requirement in re: U.S. Appl. No. 10/478,420, dated Jan. 22, 2008, 6 pages.
*Physicians Desk Reference*, 2001, 55$^{th}$ ed., Ed. Medical Economics Company, pp. 831-835.
*Physicians Desk Reference*, 2000, 54$^{th}$ ed., Ed. Medical Economics Company, p. 2457, Fig. A.
Glipizide extended release dosage information. Accessed Sep. 23, 2008 via the Internet Archive dated Apr. 17, 2001 at http://web.archive.org/web/20010417064637/http://www.rxllist.com/cgi/generic/glip_ids.htm.
Metformin dosage information. Accessed Sep. 23, 2008 via the Internet Archive dated Dec. 17, 2000 at http://web.archive.org/web/*/http://www.rxlist.com/cgi/generic/metformi_ids.htm.
PCT search report for related PCT application No. PCT/FR02/01745, dated Sep. 24, 2002.
Ge et al., "Studies on Glipizide Sustained-Release Capsules and Their Bioavailability," *Journal of China Pharmaceutical University*, [online] 2000 [retrieved on Jan. 30, 2012]: 31(5), pp. 371-374. Retrieved from the Internet: < URL: <http://en.cnki.com.cn/Article en/CJFDTotal-ZGYD200005016.htm>>. (abstract).
In the U.S. Patent and Trademark Office, Final Office Action in re: U.S. Appl. No. 10/478,420, dated Sep. 12, 2011, 18 pages.

(Continued)

*Primary Examiner* — Robert A Wax
*Assistant Examiner* — Hasan Ahmed
(74) *Attorney, Agent, or Firm* — Patton Boggs LLP (57) ABSTRACT

The invention concerns an oral galenic form for prolonged release of anti-hyperglycaemic (metformin) active principles. Said medicine enables to obtain an efficient therapeutic protection over 24 hours by overcoming the problems of bypass of the absorption window and the massive localised release of active principles. Therefor, said medicine comprises several thousand anti-hyperglycaemic (metformin) microcapsules each consisting of a core comprising at least an anti-hyperglycaemic agent and of a coating film applied on the core and enabling the prolonged release in vivo of the anti-hyperglycaemic agent. Said microcapsules have a grain size distribution ranging between 50 and 100 microns. The reproducibility of the transit kinetics and hence of bioavailability are very high. There results for the patient a lesser risk of hyperglycaemic or hypoglycaemic. The invention also concerns the preparation of said medicine and the use of a plurality of said microcapsules for making an anti-hyperglycaemic medicine. The invention is applicable to the treatment of type II diabetes.

18 Claims, 2 Drawing Sheets

OTHER PUBLICATIONS

In the U.S. Patent and Trademark Office, Non-Final Office Action in re: U.S. Appl. No. 10/478,420, dated Jan. 4, 2011, 18 pages.

In the U.S. Patent and Trademark Office, Final Office Action in re: U.S. Appl. No. 10/478,420, dated Aug. 10, 2010, 24 pages.

* cited by examiner

MEDICINE BASED ON ANTI-HYPERGLYCAEMIC MICROCAPSULES WITH PROLONGED RELEASE AND METHOD FOR PREPARING SAME

This application is a U.S. National Stage of International application PCT/FR01/03625, filed on Nov. 19, 2001.

The field of the present invention is that of oral pharmaceutical dosage forms which make possible the prolonged release of antihyperglycemic active principles. More specifically, the present invention relates to a novel medicament which can be administered by the oral route and which makes possible the prolonged release in vivo of a biguanide, such as metformin or buformin, or any pharmaceutically acceptable salt of these compounds, such as, for example, metformin hydrochloride.

The term "prolonged-release oral pharmaceutical dosage forms" is understood to mean the oral pharmaceutical dosage forms which make possible a slowed release of active principles in comparison with the conventional pharmaceutical dosage forms administered according to the same route. This definition is that given by the *European Agency for the Evaluation of Medicinal Products* in its Note on the *Quality of Modified Release Products* of 29 Jul. 1999.

This definition excludes delayed-release oral pharmaceutical dosage forms, which consist of pharmaceutical dosage forms which make it possible to delay the release of the active principles for a predetermined period of time after administration, this release, equivalent to that of the conventional pharmaceutical dosage forms, then resulting from a time lag without modification of the other pharmacokinetic parameters (Note on the *Quality of Modified Release Products* of 29 Jul. 1999, *European Agency for the Evaluation of Medicinal Products*).

The prior art comprises numerous technical proposals for producing prolonged-release forms of pharmaceutical products with the aim of extending the duration of the therapeutic coverage and of improving the comfort of the patients and the probability of them observing the dosage. However, very few studies have been devoted to developing controlled-release antihyperglycemic forms.

These antihyperglycemics, and in particular metformin hydrochloride, exhibits a low intrinsic permeability in the distal parts of the gastrointestinal tract. Its absorption therefore takes place essentially in the upper part of the gastrointestinal tract. Its oral bioavailability is of the order of 40 to 60%. It decreases when the dose increases, which suggests a saturable absorption or an absorption limited by the permeability and the transit time. Products exhibiting an absorption limited to the upper part of the gastrointestinal tract, which are said to "have an absorption window", are regarded as poor candidates for prolonged-release oral forms. The administration of these products by a conventional prolonged-release system can actually be reflected by plasma concentrations below the therapeutic threshold and thus with an ineffective treatment.

Another characteristic of these antihyperglycemics, such as metformin hydrochloride, is their very high solubility in water: more than 300 g/l at 25° C. This presents problems when it is a question of obtaining a formulation exhibiting a low and fully controlled rate of release, without sudden discharge (burst effect). To overcome this, it is generally necessary to use large amounts of polymers to form a matrix or a barrier capable of sufficiently slowing down the release of the metformin to produce the desired plasma concentration profile and, in this case, the formulator has every interest in favoring the monolithic forms, which offer less surface area to the diffusion of the active principle.

Furthermore, the daily dose of active principle can be of the order of one gram. This is the case in particular for metformin. The result of this is that the prolonged-release forms of metformin, inter alia, can be of large size. Such a large monolithic unit form can undergo random gastric emptying and can therefore remain for a poorly controlled time upstream of its absorption window. This results in a random and poorly controlled, in amount and duration, absorption of the active principle. Frequent disappointments (bypass) of this type have the consequence, in the case of antihyperglycemics, that glycemia may not be correctly controlled, which can have extremely harmful consequences for the diabetic patient.

The large monolithic pharmaceutical dosage form may also be found blocked in the twists and turns of the gastrointestinal tract. A massive and highly localized release of the active principle then occurs (dose dumping), which active principle not only will not be absorbed according to the desired profile but, moreover, is capable of causing local injuries to the tissues at the spot of the massive release.

Thus, the prior art only discloses monolithic forms capable of remaining for a certain time in the stomach (gastroretention), so as to release the metformin upstream of its absorption window.

Patent application WO 98/55107 discloses tablets comprising a matrix formed of hydrophilic polymer of high molecular weight (polyoxyethylene) comprising metformin. Once ingested, this matrix swells to large dimensions (e.g. 7.2 mm in diameter×8.8 mm in length), promoting its retention by the stomach, while limiting the rate of dissolution of the metformin.

Patent WO 99/47125 discloses a controlled-release monolithic tablet formed:
of a core comprising:
the antihyperglycemic active principle (metformin),
a water-insoluble binding agent (polyvinylpyrrolidone),
an absorption promoter (bile salt),
and of a semipermeable membrane (insoluble cellulose derivative) coating the core and pierced by at least one hole.

Conventionally, in techniques for the manufacture of tablets, the tablets according to WO 99/47125 are obtained from uncoated granules, prepared by wet granulation, that is to say agglomeration of metformin particles using the abovementioned binding agent. The granules have a size significantly greater than that of the starting metformin particles.

This pharmaceutical dosage form is supposed to have a therapeutic coverage over 24 hours after oral administration on a full stomach.

One of the disadvantages of this pharmaceutical dosage form is the presence of this absorption promoter, which can weaken the intestinal wall and can, over prolonged administration, have undesirable side effects.

Another disadvantage is that this "tablet" form has a variable gastric residence time, unlike a microparticle pharmaceutical dosage form, the residence time of which is kept in balance by the large number of particles.

Patent WO 99/47128 discloses a prolonged-release oral pharmaceutical dosage form which makes possible prolonged residence in the stomach.

It is a form suitable for active principles possessing high solubility in water and exhibiting an absorption window limited to the top part of the gastrointestinal tract (metformin). This is a two-phase system and comprises:

a particulate internal phase formed of individual granules charged with AP. The distinctive feature of these granules is that they are uncoated and comprise one or more excipients which can be:
  a hydrophobic polymer: copolymer of (meth)acrylic acid (Eudragit®), ethylcellulose,
  and/or a hydrophilic polymer: sodium carboxymethylcellulose or sodium alginate,
  and/or other hydrophobic compounds: waxes, fatty alcohols, fatty acid esters,
  and an external solid continuous phase in which the particles of the internal phase are embedded, this external continuous solid phase comprising:
  one or more hydrophilic polymers: [hydroxypropylmethylcellulose—HPMC—(with a viscosity of 5 cPs and $1 \times 10^5$ cPs), microcrystalline cellulose],
  and/or one or more hydrophobic polymers,
  and/or one or more other hydrophobic compounds (waxes, fatty alcohols, fatty acid esters).

This pharmaceutical dosage system is preferably in the form of oblong tablets. It is presented as having an increased residence time in the top part of the gastrointestinal tract (stomach/small intestine) by an effect of increase in size, without, however, achieving an upper limit resulting in blockage.

One disadvantage of this pharmaceutical dosage form is that it exhibits a variable gastric residence time, unlike a microparticle pharmaceutical dosage form, the residence time of which is kept in balance by the large number of particles.

Furthermore, it is probable that this pharmaceutical dosage system according to WO 99/47128 (preferably a tablet) has a low mechanical strength in a gastric environment. In such an event, the release of the AP would no longer be controlled.

These three inventions refer to large monolithic forms which have to be ingested as such. Thus:
  for a dose of 1 g of metformin: patent WO 98/55107 provides 8 tablets 10.4×6.6 mm present in 4 gelatin capsules;
  for a dose of 1 g of metformin: patent WO 99/47128 provides 2 large oblong tablets;
  for a dose of 850 mg of metformin: patent WO 99/47125 provides a tablet with a diameter of 12 mm.

Problems of observance may be encountered with these forms for patients having difficulties in swallowing.

Furthermore, the plasma concentration profile obtained from these systems is highly conditioned by the residence time in the stomach, which can be the subject of large interindividual variations. The monolithic systems are subject to and sometimes accentuate the effect of these interindividual variations, which can result in the treatment being ineffective in a not insignificant portion of the population treated.

Finally, these pharmaceutical dosage systems are capable of resulting either in problems of bypass of the absorption window or in problems of localized accumulation of the active principle, and of subsequent injuries.

PCT Application WO 96/11675 discloses medicinal and/or nutritional microcapsules for the administration per os of active principle, with the exception of aspirin and without any details of a specific class of active principles, namely antihyperglycemics and in particular metformin. These medicinal microcapsules are composed of particles of active principle (without antihyperglycemics being specified), each covered with a coating film comprising at least one film-forming polymer P1, at least one nitrogenous polymer P2, at least one plasticizer and at least one surfactant and/or lubricant. The medicinal microcapsules according to WO 96/11675 do not solve the specific problem of the therapeutic coverage over 24 hours of antihyperglycemics and with an absorption window in the top parts of the gastrointestinal tract, which are very soluble in water and which have to be ingested at high doses each time they are taken (1 g per day).

The document WO 00/28989 discloses delayed-release compositions which are provided in the form of gelatin capsules comprising multiple cores of granules comprising an insulin sensitization agent and another antidiabetic agent, which can be a biguanide, such as metformin. The cores of granules can be coated with an enteric composition and in particular a composition composed of a film-forming polymer, such as Eudragit L100-55. However, this document does not disclose an antihyperglycemic medicament which can be administered per os, which is provided in the form of microparticles which make possible the prolonged release of the antihyperglycemic active principle or principles.

In such a state of the art, one of the essential objectives of the present invention is to provide a novel pharmaceutical dosage system for the oral administration of antihyperglycemic active principles, this system having to make it possible to obtain an effective therapeutic coverage over 24 hours while overcoming the problems of bypass of the absorption window and of massive localized release of active principle.

One objective of the present invention is to provide a pharmaceutical form composed of a large number, of the order of several thousand, of antihyperglycemic microcapsules and in particular metformin microcapsules, this multiplicity of microcapsules statistically providing good reproducibility of the kinetics of transit of the antihyperglycemic (metformin) throughout the gastrointestinal tract. This results in better control of the bioavailability and thus, for the patient, in a reduced risk of hyperglycemia or of hypoglycemia.

One objective of the present invention is to provide a prolonged-release antihyperglycemic, and in particular metformin, multimicrocapsule pharmaceutical dosage form, this pharmaceutical dosage form being composed of a tablet which is dispersible in a liquid or in the mouth, of an effervescent tablet or of powder in sachets.

Another objective of the present invention is to provide a prolonged-release antihyperglycemic, and in particular metformin, multimicrocapsule form which results, after oral administration, in a plasma peak after more than 6 hours approximately.

Another objective of the present invention is to provide a prolonged-release antihyperglycemic, and in particular metformin, multimicrocapsule form, the bioavailability of this not being reduced by administration on a full stomach.

Another objective of the present invention is to provide a prolonged-release antihyperglycemic, and in particular metformin, multimicrocapsule form which provides sufficient therapeutic coverage for administration of the active principle once or twice daily.

Another object of the present invention is to obtain a multimicrocapsule system which provides for the in vitro release of the antihyperglycemic products over more than 8 hours while avoiding the use of large amounts of polymers, the active principle content remaining comparable to, indeed even greater than, that of monolithic forms.

Another object of the present invention is to provide a simple and economic process for the preparation of the abovementioned multimicrocapsule pharmaceutical dosage form.

The objectives stated above, among others, are obtained by the invention, which provides, first, a medicament based on at least one antihyperglycemic which can be administered by the oral route, characterized:

in that it comprises a plurality of microcapsules each composed of a core comprising at least one antihyperglycemic and of a coating film applied to the core and which makes possible the prolonged release in vivo of the antihyperglycemic(s), with the exclusion of the coating films composed of enteric compositions and of the coating films with the composition following:

1—at least one film-forming polymer (P1) which is insoluble in the fluids of the tract, present in a proportion of 50 to 90%, preferably 50 to 80%, by weight on a dry basis with respect to the total mass of the coating composition and composed of at least one water-insoluble cellulose derivative of cellulose, namely ethylcellulose and/or cellulose acetate;

2—at least one nitrogenous polymer (P2), present in a proportion of 2 to 25%, preferably 5 to 15%, by weight on a dry basis with respect to the total mass of the coating composition and composed of at least one polyacrylamide and/or one poly-N-vinylamide and/or one poly-N-vinyllactam, namely polyacrylamide and/or polyvinylpyrrolidone;

3—at least one plasticizer, present in a proportion of 2 to 20%, preferably of 4 to 15%, by weight on a dry basis with respect to the total mass of the coating composition and composed of at least one of the following compounds: glycerol esters, phthalates, citrates, sebacates, esters of cetyl alcohol, castor oil, salicylic acid and cutin;

4—and optionally at least one surface-active and/or lubricating agent, present in a proportion of 2 to 20%, preferably of 4 to 15%, by weight on a dry basis with respect to the total mass of the coating composition and chosen from anionic surfactants, namely alkali metal or alkaline earth metal salts of fatty acids, stearic acid and/or oleic acid being preferred, and/or from nonionic surfactants, namely polyoxyethylenated sorbitan esters and/or polyoxyethylenated castor oil derivatives, and/or from lubricating agents, such as calcium stearate, magnesium stearate, aluminum stearate or zinc stearate, or such as sodium stearylfumarate and/or glycerol behenate; it being possible for said agent to comprise just one or a mixture of abovesaid products;

in that these microcapsules have a particle size of between 50 and 1000 microns, preferably between 100 and 750 microns and more preferably still between 200 and 500 microns.

The term "enteric compositions" is understood to mean the compositions which confer on the coating a resistance to acidic pH (gastric pH) and which make possible release of the active principle or principles when the pH is raised.

Thus, the medicament according to the invention is particularly suitable for antihyperglycemic active principles which have the characteristic of having an absorption window situated in the top parts of the gastrointestinal tract (stomach and start of the small intestine), which are very soluble in water and for which the dosage is of the order of 1 g per day, which requires the ingestion of a large amount of product each time it is taken.

This medicament, in a "multimicrocapsule" pharmaceutical dosage form composed of a plurality of microcapsules, necessarily restricts, for statistical reasons, the risk of bypass of the absorption window and eliminates the risk of localized accumulation of active principle. This results in an optimum absorption of antihyperglycemics in the absorption window, in an amount such that and over a time such that the therapeutic coverage can be guaranteed over at least 12 h with all the therapeutic safety desirable (control of glycemia). This is because the large number of particles (e.g. of the order of 10 000) makes possible a reproducible distribution, thus reducing the risks of hyper- and hypoglycemia.

The antihyperglycemics more particularly affected by the invention are those chosen within the group consisting of metformin and its salts, such as metformin hydrochloride.

Figure 1:
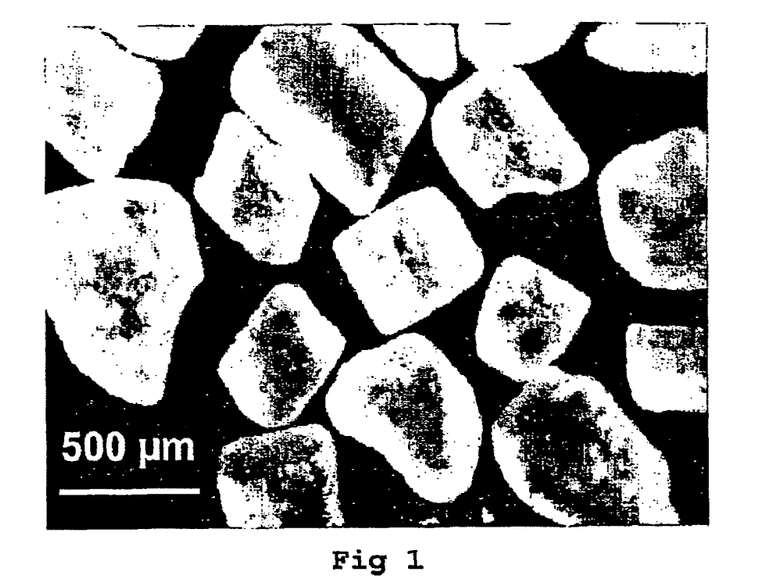
FIGS. 1 and 2 are photographs of microcapsules respectively before and after the dissolutest dissolution test employed and defined in the examples.
Figure 2:
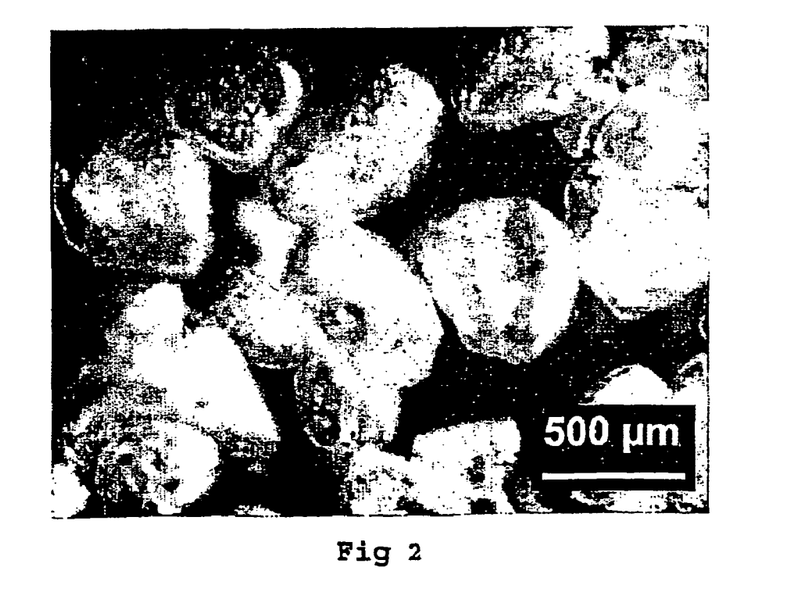

The appended FIGS. 1 and 2 are photographs (respectively before and after a dissolution test, cf. examples below) on several constituent microcapsules of the medicament according to the invention. These photos clearly show that each individual microcapsule comprises a core wrapped in a coating film which controls the prolonged release of the antihyperglycemic active principle or principles.

The size of each microcapsule is less than 1 mm and in practice between 200 and 500 μm, as is apparent in the photo of FIG. 1. It should be emphasized that this is not a matter of an agglomerate of particles of antihyperglycemics in granules with a size of greater than 1 mm and for which the matrix is formed by a polymer binder.

The medicament according to the invention relates to dry pulverulent forms or forms in suspension in a liquid or alternatively forms disintegrated in the mouth or in a liquid.

In fact, the medicament according to the invention can be categorized as a novel "multimicrocapsule" pharmaceutical dosage system intended to be easy to administer per os and which makes possible prolonged release in vivo, guaranteeing therapeutic coverage of at least 12 hours and, preferably, over at least 24 hours.

The size and the coating of the microcapsules are preferably chosen so that, everything else otherwise being equal, its bioavailability during oral administration on a full stomach is at least equal to its bioavailability during oral administration on an empty stomach.

According to a preferred characteristic of the invention, the coating film for the microcapsules is designed so that, after ingestion of a given dose of antihyperglycemic, the time (Tmax) corresponding to the maximum plasma concentration in the curve of the plasma concentration as a function of time is greater than or equal to 6 hours, and the bioavailability, given by the area under the curve (AUC), is greater than or equal to 60%, preferably 80%, with respect to that obtained with the same dose of immediate-release antihyperglycemic.

Curves of this type, which give the plasma concentration as a function of time elapsed after ingestion, describe the therapeutic coverage and the therapeutic effectiveness of the medicament. There are grounds for recording that they are entirely satisfactory for the multimicrocapsule and antihyperglycemic medicament according to the invention.

Thus, the medicament according to the invention offers entirely advantageous prospects in the treatment of type II diabetes, alone or in combination with other antidiabetic medicaments, such as insulin.

In an entirely surprising and unexpected way, the oral multimicrocapsule pharmaceutical dosage system according to the invention does not require the use of large amounts of excipient polymers in relation to the mass of antihyperglycemics. Contrary to the situation for known pharmaceutical dosage systems of monolithic type with large dimensions.

Thus, according to an advantageous provision of the invention, the mean fraction by mass of antihyperglycemic in the microcapsules is greater than 50%, preferably greater than or equal to 60%.

The technical problems solved by the invention are more specifically those encountered for antihyperglycemics and in particular those chosen from biguanides, preferably from the group of biguanides comprising metformin and buformin and their salts, metformin and its salts being particularly preferred.

The medicament according to the invention can also be defined by characteristics of in vitro release of the antihyperglycemic(s), by dissolution in an aqueous medium of the coating film. From which it results that, in an in vitro dissolution test known as the type II dissolutest in accordance with the Pharmacopoeia, the dissolution of the antihyperglycemic extends over at least 8 hours, preferably at least 20 hours.

The multimicrocapsule medicament according to the invention can exist in various pharmaceutical dosage forms, including in particular:
  tablets which can disintegrate in the mouth,
  tablets which can disintegrate by effervescence in a liquid (water),
  tablets which can disintegrate in a liquid (water),
  powders of given doses packaged in sachets,
  suspensions of microcapsules in a liquid (water),
  gelatin capsules comprising a powder formed of microcapsules.

According to a specific but nonlimiting embodiment of the invention, the multimicrocapsule medicament is composed of a pharmaceutical dosage form, the dose of antihyperglycemic of which is between 800 and 1200 mg, preferably between 900 and 1100 mg and more preferably still of the order of 1000 mg.

Such a dose is particularly suitable for the treatment of type II diabetes, according to an effective dosage which makes it possible to contribute to maintaining glycemia at acceptable levels 24 hours after the medicament has been taken.

This multimicrocapsule medicament, the antihyperglycemic dose of which is between 800 and 1200 mg, preferably between 900 and 1100 mg and more preferably still of the order of 1000 mg, is advantageously composed of several thousand microcapsules as defined above, this multiplicity providing good reproducibility of the gastrointestinal transit of the antihyperglycemic, thus reducing the risk to the patient of hypo- or hyperglycemia.

To give a few details of the structure of the microcapsules, it is specified that the core of said microcapsules can be, for example, a granule comprising antihyperglycemic and granulation excipients and/or a particle of antihyperglycemic, preferably a monocrystal.

In the core of the microcapsules, the antihyperglycemic can be used in combination with one or more excipients. This is in particular the case when the core is composed of a granule. The excipients then employed are those which are conventional in granulation.

In practice, the film coating deposit on each granule can be composed of one or more film-forming macromolecules well known to a person skilled in the art for preparing prolonged-release forms. For example, and without the list being exhaustive, it can be chosen from the following families: cellulose ethers, cellulose ethers/esters, cellulose esters, cellulose diesters, cellulose triesters, cellulose acylate, cellulose diacylate, cellulose triacylate, cellulose diacetate and triacetate, cellulose acetate/propionate, cellulose acetate/butyrate, polymethacrylates, waxes and vinyl acetate copolymers.

Preferably, the film-forming macromolecule is ethylcellulose, Eudragit® RS, Eudragit® RL or cellulose acetate.

More preferably still, use will be made of the combinations of cellulose derivatives and of at least one pharmaceutically acceptable hydrophilic polymer.

The fraction by mass of cellulose derivatives is advantageously between 30 and 90% and more advantageously still between 50 and 80%.

The film coating can also comprise the excipients commonly used as plasticizers. They can be chosen from the following nonexhaustive list: tributyl acetylcitrate, triethyl acetylcitrate, acetylated glycerides, castor oil, dibutyl phthalate, diethyl phthalate, diethyl sebacate, dibutyl sebacate, dimethyl phthalate, glycerol, glycerol monostearate, glyceryl triacetate, polyethylene glycol, polyoxyethylene/polyoxypropylene copolymers, propylene glycol, tributyl citrate, triethyl citrate, adipate, azelate, enzoate, citrate, citric acid esters, triacetin, vegetable oils, glycerin sorbitol, diethyl oxalate, diethyl malate, diethyl fumarate, dibutyl succinate, diethyl malonate, dioctyl phthalate or glycerol tributyrate.

Other commonly used excipients can be introduced into the coating, such as soluble or insoluble fillers (talc, inorganic salts, sugars, polyvinylpyrrolidone, polyethylene glycol, and the like), lubricants, dyes or pigments.

According to another of its aspects, the invention is targeted at the process for the preparation of the medicament as defined above.

This process consists:
  in employing granules comprising antihyperglycemic(s) and granulation excipients or alternatively particles of substantially pure antihyperglycemic(s), preferably monocrystals of antihyperglycemic(s);
  and in then spraying, over these granules and/or these particles, a coating solution comprising one or more products selected from the group consisting of:
    film-forming macromolecules, preferably chosen from the group consisting of:
      cellulose ethers, cellulose ethers/esters, cellulose esters, cellulose diesters, cellulose triesters, cellulose acylate, cellulose diacylate, cellulose triacylate, cellulose diacetate and triacetate, cellulose acetate/propionate, cellulose acetate/butyrate, polymethacrylates, waxes and vinyl acetate copolymers;
      ethylcellulose, Eudragit® RS, Eudragit® RL and cellulose acetate being particularly preferred;
    plasticizers, preferably chosen from the following nonexhaustive list: tributyl acetylcitrate, triethyl acetylcitrate, acetylated glycerides, castor oil, dibutyl phthalate, diethyl phthalate, diethyl sebacate, dibutyl sebacate, dimethyl phthalate, glycerol, glycerol monostearate, glyceryl triacetate, polyethylene glycol, polyoxyethylene/polyoxypropylene copolymers, propylene glycol, tributyl citrate, triethyl citrate, adipate, azelate, enzoate, citrate, citric acid esters, triacetin, vegetable oils, glycerin sorbitol, diethyl oxalate, diethyl malate, diethyl fumarate, dibutyl succinate, diethyl malonate, dioctyl phthalate or glycerol tributyrate;
    and optionally other excipients selected from soluble or insoluble fillers (talc, inorganic salts, sugars, polyvinylpyrrolidone, polyethylene glycol, and the like), lubricants, dyes or pigments;
using a technology provided for this purpose and known to a person skilled in the art, such as that involving a Wurster® system from Glatt or a Precisiocoater® system from Aeromatic.

As already indicated above, the granules capable of forming the core of the microcapsules are obtained by conventional granulation techniques.

The granulation excipients employed are well known to a person skilled in the art and are in particular those exemplified above.

The innovative characteristics of the process result from the materials employed and from the combination of the carefully selected physical parameters.

In accordance with the invention, provision is also made, as solution to the problems mentioned at the beginning of the present account, namely: bypass of the absorption window, massive and localized release of the antihyperglycemic, pharmaceutical dosage form which can be easily swallowed, everything from the viewpoint of effective and certain therapeutic coverage for at least 12 h (control of glycemia), to use a plurality of microcapsules:

each composed of a core comprising at least one antihyperglycemic and of a coating film applied to the core and which makes possible the prolonged release in vivo of the antihyperglycemic(s), and having a particle size of between 50 and 1000 microns, preferably between 100 and 750 microns and more preferably still between 200 and 500 microns;

for manufacturing a medicament based on at least one antihyperglycemic which can be administered by the oral route, which can be easily swallowed and which contributes to the control of glycemia (reduction in the risk of hypo- or hyperglycemia) over at least 12 h in a reliable manner, while limiting problems of bypass, of accumulation and of localized and massive release of antihyperglycemic.

According to yet another of its subject matters, the present invention relates to a method for the treatment of type II diabetes, in which recourse is had to a medicament as defined above as product per se or as product obtained by the process described above.

The examples which follow will make possible a better understanding of the invention and an apprehension of all these advantages and all its alternative embodiments.

EXAMPLES

EXAMPLE 1

159.5 g of stearic acid and 159.5 g of ethylcellulose are dissolved in 2870 g of isopropanol maintained at 50° C. This solution is sprayed over 700 g of metformin.HCl crystals with a mean diameter of between 100 and 200 µm charged to a Glatt GPCG1 spray coater. The film-coating conditions are: product temperature: 38-42° C., rate of spraying: 10 g/min, atomization pressure: 2 bar.

The microcapsules obtained were tested in a type II dissolutest in accordance with the Pharmacopoeia in a $KH_2PO_4$/NaOH buffer medium at pH 6.8, maintained at 37° C. and stirred at 10 revolutions/min.

It turns out that the microcapsules were not modified externally by the dissolution test. This proves that they indeed comprise a coating through which the metformin diffused during the dissolution test and which was not affected by the dissolution.

The dissolution profile obtained is as follows:

TABLE 1

| Time (hour) | Metformin dissolved (%) |
|---|---|
| 2 | 14.7 |
| 4 | 34.4 |
| 8 | 69.4 |
| 12 | 87.5 |
| 16 | 94.3 |
| 20 | 97.1 |

Figure 3:
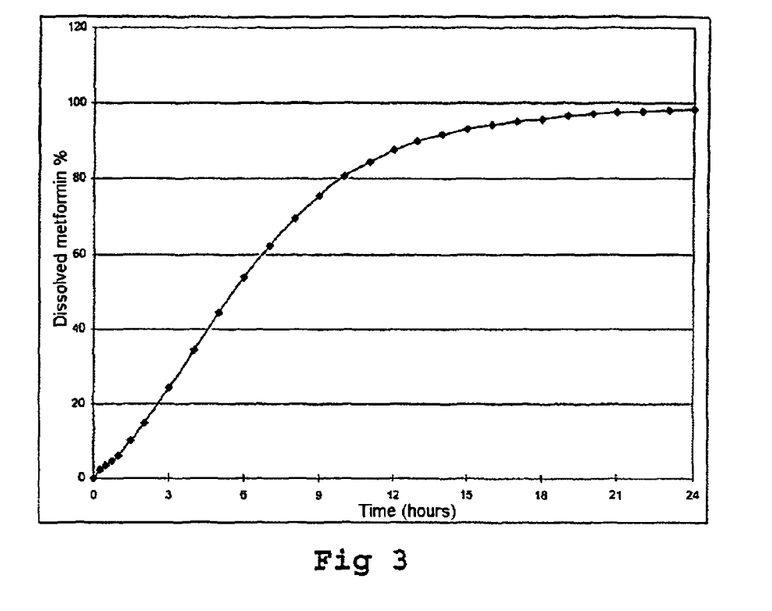
FIG. 3 is a curve giving the percentage of dissolution (dissolutest) as a function of time of metformin microcapsules according to example 1.

The dissolution profile of the product prepared in this example is represented in FIG. 3.

EXAMPLE 2

51.13 g of ethylcellulose and 5.73 g of castor oil are dissolved in a mixture of 393 g of acetone and 262 g of isopropanol. This solution is sprayed over 200 g of metformin.HCl crystals with a mean diameter of between 200 and 500 µm charged to a Niro CC1 spray coater. The film-coating conditions are: product temperature: 38-42° C., rate of spraying: 4 g/min, atomization pressure: 1 bar.

The microcapsules obtained were tested in a type II dissolutest in accordance with the Pharmacopoeia in a $KH_2PO_4$/NaOH buffer medium at pH 6.8, maintained at 37° C. and stirred at 10 revolutions/min.

The dissolution profile obtained is as follows:

TABLE 2

| Time (hour) | Metformin dissolved (%) |
|---|---|
| 2 | 29.4 |
| 4 | 56.0 |
| 8 | 85.2 |
| 12 | 93.6 |
| 16 | 96.9 |
| 20 | 98.7 |

Figure 4:
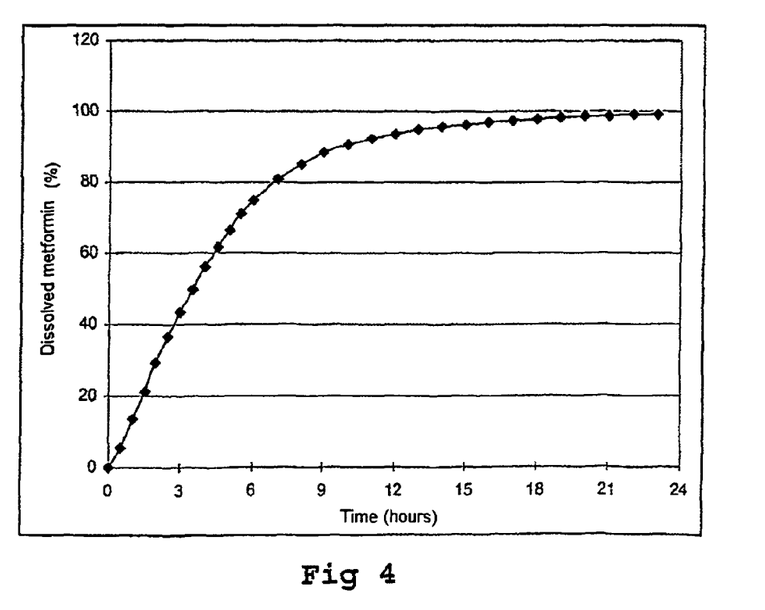
FIG. 4 is a curve giving the percentage of dissolution (dissolutest) as a function of time of metformin microcapsules according to example 2.

The dissolution profile of the product prepared in this example is represented in FIG. 4.

EXAMPLE 3

Two gelatin capsules with a size of 00, each comprising 500 mg of coated metformin in the microcapsules described in example 2, or else 4 Glucophage tablets, each comprising 250 mg of metformin, are administered to 12 healthy subjects after eating with 250 ml.

Blood samples are taken at 0, 0.5, 1, 2, 3, 4, 5, 6, 8, 10, 12, 16, 20, 24 and 36 hours after administration in order to analyze the metformin concentration.

The mean plasma concentration profile demonstrates an increase in the time corresponding to the plasma concentration maximum, this being achieved without a very significant decrease in the bioavailability evaluated by the area under the plasma concentration profile between the points and 36 hours.

The main pharmacokinetic parameters are listed in table 3 below.

TABLE 3

|  | Tmax (h) | Cmax (ng/ml) | AUC 0–36 h (ng · h/ml) | Relative bioavailability (%) |
| --- | --- | --- | --- | --- |
| Glucophage | 3.5 | 1280 | 10 500 | 100 |
| Microcapsules of example 2 | 7.1 | 1015 | 9660 | 92 |

The microcapsules of the invention thus represent a significant overhang in the field of the administration of metformin by the oral route for the treatment of diabetes.

The invention claimed is:

1. A medicament based on at least one biguanide antihyperglycemic agent which is administered by the oral route,
    wherein the medicament comprises a plurality of microcapsules for oral administration;
    wherein the microcapsules have a particle size between 50 and 750 microns;
    wherein the microcapsules have a core comprising at least one biguanide antihyperglycemic agent;
    wherein the mean fraction by mass of the biguanide in the microcapsules is greater than 50%;
    wherein the microcapsules are coated with a coating film adapted to prolong the release in vivo of the biguanide antihyperglycemic agent and to extend over at least 8 hours the dissolution of the biguanide antihyperglycemic agent in an in vitro dissolution test;
    wherein the coating film comprises at least one film-forming macromolecule and at least one plasticizer;
    wherein the film forming macromolecules are selected from the group consisting of: cellulose ethers, cellulose ethers/esters, cellulose esters, cellulose diesters, cellulose triesters, cellulose acylate, cellulose diacylate, cellulose triacylate, cellulose diacetate and triacetate, cellulose acetate/propionate, cellulose acetate/butyrate, polymethacrylates, waxes, vinyl acetate copolymers, and mixtures thereof;
    wherein the plasticizers are selected from the group consisting of: tributyl acetylcitrate, triethyl acetylcitrate, acetylated glycerides, castor oil, dibutyl phthalate, diethyl phthalate, diethyl sebacate, dibutyl sebacate, dimethyl phthalate, glycerol, glycerol monostearate, glyceryl triacetate, polyethylene glycol, polyoxyethylene/polyoxypropylene copolymers, propylene glycol, tributyl citrate, triethyl citrate, adipate, azelate, enzoate, citrate, citric acid esters, vegetable oils, glycerin sorbitol, diethyl oxalate, diethyl malate, diethyl fumarate, dibutyl succinate, diethyl malonate, dioctyl phthalate, glycerol tributyrate, and mixtures thereof;
    wherein the coating film is not an enteric composition; and
    wherein the coating film does not have a nitrogenous polymer, present in a proportion of 2 to 25%, by weight on a dry basis with respect to the total mass of the coating composition and composed of at least one polyacrylamide, and/or one poly-N-vinylamide and/or one poly-N-vinyllactam.

2. The medicament according to claim 1, wherein the size and the coating of the microcapsules are chosen so that the medicament's bioavailability during oral administration on a full stomach is at least equal to its bioavailability during oral administration on an empty stomach.

3. The medicament according to claim 1, wherein the antihyperglycemic is a biguanide selected from the group consisting of: metformin, buformin, metformin salts, and buformin salts.

4. The medicament according to claim 1, wherein the dissolution of the biguanide antihyperglycemic agent extends over at least 8 hours, in an in vitro dissolution test known as the type II dissolutest in accordance with the Pharmacopoeia.

5. The medicament according to claim 1, wherein the form of the medicament is selected from the group consisting of: a tablet which can disintegrate in the mouth, a tablet which can disintegrate in a liquid, a powder, a suspension and a gelatin capsule.

6. The medicament according to claim 1, wherein the total dose of biguanide antihyperglycemic agent in the medicament is between 800 and 1200 mg.

7. The medicament according to claim 1, wherein the medicament comprises at least one thousand of the microcapsules.

8. The medicament according to claim 1, wherein the core of the microcapsules is a granule comprising said biguanide antihyperglycemic agent and granulation excipients.

9. The medicament according to claim 8 wherein the core of the microcapsules is a monocrystal of biguanide antihyperglycemic agent.

10. The medicament according to claim 1 wherein the coating film comprises one or more products selected from the group consisting of: soluble fillers, insoluble fillers, lubricants, dyes, pigments, and mixtures thereof.

11. The medicament according to claim 1, wherein the film-forming macromolecules are selected from the group consisting of ethylcellulose, ammonio methacrylate copolymer Type B, ammonio methacrylate copolymer Type A, cellulose acetate, and mixtures thereof.

12. The medicament according to claim 1, wherein the film-forming macromolecules comprise-cellulose derivatives and at least one pharmaceutically acceptable hydrophilic polymer.

13. The medicament according to claim 12, wherein the fraction by mass of cellulose derivatives is between 30 and 90%.

14. A method for the preparation of the medicament of claim 1, wherein the method consists of:
    creating granules comprising biguanide antihyperglycemic agent;
    and then spraying, over these granules a coating solution comprising film-forming macromolecules and plasticizers,
    wherein the coating film is not an enteric composition; and
    wherein the coating film does not have a nitrogenous polymer, present in a proportion of 2 to 25%, by weight on a dry basis with respect to the total mass of the coating composition and composed of at least one polyacrylamide, and/or one poly-N-vinylamide and/or one poly-N-vinyllactam;
    such that the resulting microparticle is 50 to 1000 microns in diameter.

15. The method according to claim 14, wherein the coating solution comprises other excipients selected from the group consisting of: soluble fillers insoluble fillers, lubricants, dyes, pigments, and mixtures thereof.

16. A method for administering an orally administered medicament based on at least one biguanide anti-hyperglycemic agent which can be easily swallowed and which contributes to the control of glycemia over at least 12 h in a reliable manner and while limiting problems of bypass, of accumulation and of localized and massive release of biguanide antihyperglycemic agent, said method consisting in using a plurality of microcapsules;
    wherein each microcapsule is composed of a core comprising at least one antihyperglycemic;

wherein a coating film comprising at least one film-forming macromolecule and at least one plasticizer is applied to the core to prolong the release in vivo of the antihyperglycemic agent, wherein the coating film is adapted to prolong the release in vivo of the biguanide antihyperglycemic agent and to extend over at least 8 hours the dissolution of the biguanide antihyperglycemic agent in an in vitro dissolution test;

wherein the final particle size of the microcapsule is between 50 and 750 microns;

wherein the mean fraction by mass of the biguanide in the microcapsules is greater than 50%;

wherein the film forming macromolecules are selected from the group consisting of: cellulose ethers, cellulose ethers/esters, cellulose esters, cellulose diesters, cellulose triesters, cellulose acylate, cellulose diacylate, cellulose triacylate, cellulose diacetate and triacetate, cellulose acetate/propionate, cellulose acetate/butyrate, polymethacrylates, waxes, vinyl acetate copolymers, and mixtures thereof;

wherein the plasticizers are selected from the group consisting of: tributyl acetylcitrate, triethyl acetylcitrate, acetylated glycerides, castor oil, dibutyl phthalate, diethyl phthalate, diethyl sebacate, dibutyl sebacate, dimethyl phthalate, glycerol, glycerol monostearate, glyceryl triacetate, polyethylene glycol, polyoxyethylene/polyoxypropylene copolymers, propylene glycol, tributyl citrate, triethyl citrate, adipate, azelate, enzoate, citrate, citric acid esters, vegetable oils, glycerin sorbitol, diethyl oxalate, diethyl malate, diethyl fumarate, dibutyl succinate, diethyl malonate, dioctyl phthalate, glycerol tributyrate, and mixtures thereof;

wherein the coating film is not an enteric composition;

wherein the coating film does not have a nitrogenous polymer, present in a proportion of 2 to 25%, by weight on a dry basis with respect to the total mass of the coating composition and composed of at least one polyacrylamide, and/or one poly-N-vinylamide and/or one poly-N-vinyllactam; and wherein when the medicament is administered, the blood glycemia over at least 12 hour is controlled while decreasing the problems of bypass, accumulation and localized and massive release of biguanide anti-hyperglycemic agent.

17. A method for the treatment of type II diabetes, in which the method comprises administering to a patient with type II diabetes therapeutic amount of the medicament of claim 16.

18. A method for the treatment of type II diabetes, in which the method comprises administering to a patient with type II diabetes a therapeutic amount of the medicament of claim 14.

* * * * *